United States Patent [19]

Beatty

[11] 4,321,253

[45] Mar. 23, 1982

[54] SUSPENSION OF MICROENCAPSULATED BACAMPICILLIN ACID ADDITION SALT FOR ORAL, ESPECIALLY PEDIATRIC, ADMINISTRATION

[76] Inventor: Morgan L. Beatty, Pfizer Inc., 235 E. 42nd St., New York, N.Y. 10017

[21] Appl. No.: 180,537

[22] Filed: Aug. 22, 1980

[51] Int. Cl.³ .................... A61K 9/50; A61K 31/43; A61K 9/14
[52] U.S. Cl. ........................................ 424/35; 424/271
[58] Field of Search .................................. 424/35, 271

[56] References Cited

U.S. PATENT DOCUMENTS

| | | | |
|---|---|---|---|
| 3,549,746 | 12/1970 | Granatek et al. | 424/35 |
| 3,873,521 | 3/1975 | Ekstrom et al. | 424/271 |
| 4,016,254 | 4/1977 | Seager | 424/80 |
| 4,101,651 | 7/1978 | Kobayashi et al. | 424/35 |
| 4,127,647 | 12/1978 | Sato et al. | 424/35 |
| 4,177,254 | 12/1979 | Khan et al. | 424/35 |

FOREIGN PATENT DOCUMENTS 2118999 8/1972 France.
1479655 7/1977 United Kingdom.

OTHER PUBLICATIONS

Rozencweig et al., Clin. Pharm. Therap. 19(5PT.): 592–597 (1976), Antibacteriyl Activity and Pharmaco Kinetics of Bacampicillin and Ampicillin.
Bodin et al., Antimicrobial Agents & Chemotherapy 8(5):518–525 (1975) Bacampicillin: A New Orally Well-Absorbed Derivative of Ampicillin.
Taskis Chem. Abstr. 84:8940m (1976) of Ger. Off. 2 509 572 Sep. 11, 1975, 14 pp.
Seager Chem. Abstr. 78:33916s (1973) of Ger. Off 2 164 019, Aug. 3, 1972, 24 pp.
Ekstrom, Chem. Abstr. 80:14921q (1974) of Ger. Off. 2 311 328, Oct. 18, 1973, 84 pp.
Swahn, Chem. Abstr. 84:159464k (1976) of Eur. J. Clin. Pharmacol., 1976 9(4):299–306, "Gastro-Intestinal Absorption and Metabolism of Two 35S-Labelled Ampicillin Esters" (Pivampicillin) and (Carampicillin).

*Primary Examiner*—Shep K. Rose
*Attorney, Agent, or Firm*—Francis X. Murphy; Charles J. Knuth; Lawrence C. Akers

[57] ABSTRACT

A novel formulation of bacampicillin for oral administration is disclosed. Microcapsules comprising an acid addition salt of bacampicillin coated with a mixture of ethyl cellulose:water-soluble or water-permeable filler material are suspended in a buffered vehicle having a pH of at least 6.9. The novel suspension is characterized by palatable taste, surprisingly good stability and enhanced bioavailability after oral administration. The novel suspension is well suited for multiple dose oral administration. The preferred filler material is hydroxypropyl cellulose.

12 Claims, No Drawings

SUSPENSION OF MICROENCAPSULATED BACAMPICILLIN ACID ADDITION SALT FOR ORAL, ESPECIALLY PEDIATRIC, ADMINISTRATION

BACKGROUND OF THE INVENTION

D-(−)-alpha-aminobenzylpenicillin (ampicillin) has been widely used as an antibacterial agent, especially in pediatric applications, because of its broad spectrum activity and suitability for oral administration. Administration of bacampicillin, the 1′-ethoxycarbonyloxyethyl ester of ampicillin, results in higher blood levels of ampicillin than when ampicillin itself is administered orally (see U.S. Pat. No. 3,873,521 and Bodin et al., *Antimicrobial Agents and Chemotherapy*, 8 (5), pp. 518–525 (1975)). The free base of bacampicillin is difficult to prepare, unstable and insoluble in water, thus rendering its oral administration impractical. The pharmaceutically acceptable acid addition salts of bacampicillin, e.g., the hydrochloride salt, are generally water-soluble. Unfortunately, such water-soluble acid addition salts possess an objectionable taste which renders the product unacceptable for pediatric use.

Conventional taste masking techniques, such as the addition of sweeteners and flavoring agents, are not capable of adequately masking the strong taste of bacampicillin acid addition salts. In one prior art technique, bacampicillin hydrochloride has been microencapsulated with a coating of ethyl cellulose and the microcapsules combined with solid vehicle ingredients in a sachet. The contents of the sachet are mixed with water to constitute a dilute single dosage suspension having a pH of about 5. Even if swallowed immediately after reconstitution, a strong bacampicillin hydrochloride taste is experienced which can be highly objectionable to an infant patient. Use of this prior art reconstituted suspension for multiple dose administration is not feasible because of the taste problem.

It is known that drugs can be microencapsulated for taste-masking purposes with a coating of a mixture of ethyl cellulose and hydroxypropyl cellulose, with the microcapsules then reconstituted as a suspension. However, the prior art does not reveal any successful application of this or any other coating procedure to the problem of preparing a stable suspension of a bacampicillin acid addition salt with palatable taste and good bioavailability.

SUMMARY OF THE INVENTION

It is an object of the present invention to prepare an aqueous oral formulation of an acid addition salt of bacampicillin having (1) enhanced bioavailability, i.e., rapid and efficient absorption of the active ingredient from the intestinal tract, (2) a taste making it palatable for pediatric use, and (3) satisfactory stability so that the aqueous formulation may be administered after reconstitution in multiple doses to a patient over a period of days with substantial maintenance of potency, palatable taste and bioavailability.

The above-mentioned and other objects of the invention are achieved with a novel powder capable of being reconstituted by addition of water to yield a pharmaceutical suspension of bacampicillin acid addition salt microcapsules in an aqueous suspension medium, said powder comprising a mixture of bacampicillin acid addition salt microcapsules and a plurality of pharmaceutically acceptable suspension vehicle ingredients, said microcapsules comprising a core of a pharmaceutically acceptable, water-soluble acid addition salt of bacampicillin and a coating thereon consisting essentially of a mixture of a major portion of ethyl cellulose and a minor portion of a pharmaceutically acceptable, water-soluble or water-permeable filler material, said vehicle being such that the pH of the aqueous suspension medium in said reconstituted pharmaceutical suspension is at least 6.9, and the weight ratio of ethyl cellulose to said filler material in said coating being such that said pharmaceutical suspension has a stability of at least 85% retention of potency after 14 days at about 3° C., and provides an average maximum blood serum ampicillin level of at least about 6 micrograms/ml. after oral administration thereof to adult humans. The scope of the present invention also includes an aqueous pharmaceutical suspension prepared by admixing said novel powder with water.

The pharmaceutically acceptable filler material may be, e.g., sodium chloride or propylene glycol, but is preferably an organic polymeric material. More preferably, the filler material is selected from the group consisting of hydroxypropyl cellulose, low substituted hydroxypropyl cellulose having a hydroxypropyl content of about 7 to 14 weight percent, methyl cellulose, hydroxypropyl methyl cellulose, polyethylene glycol, polyvinyl alcohol, carboxymethyl cellulose, polyvinyl pyrrolidone, gelatin, gum arabic and corn starch. The highly desirable combination of properties of the reconstituted pharmaceutical suspension of this invention, i.e., bioavailability, taste-masking and stability, is realized only when the critical limitation on suspension medium pH is satisfied. Additionally, the ratio of ethyl cellulose to filler material in the coating must fall within a specific range, which range will depend upon the particular filler material utilized.

The preferred embodiment of the present invention is a novel powder capable of being reconstituted by addition of water to yield a pharmaceutical suspension of bacampicillin acid addition salt microcapsules in an aqueous suspension medium, said powder comprising a mixture of bacampicillin acid addition salt microcapsules and a plurality of pharmaceutically acceptable suspension vehicle ingredients, said microcapsules comprising a core of a pharmacuetically acceptable, water-soluble acid addition salt of bacampicillin and a coating thereon consisting essentially of a mixture of ethyl cellulose and hydroxypropyl cellulose in a weight ratio of from about 1.5:1 to about 2:1, and said vehicle ingredients being such that the pH of the aqueous suspension medium in said reconstituted pharmaceutical suspension is at least 6.9, and an aqueous pharmaceutical suspension prepared by admixing said novel powder with water.

DETAILED DESCRIPTION OF THE INVENTION

The composition of this invention may be commercially distributed in dry powder form, i.e., for reconstitution by a pharmacist by addition of water to form the novel suspension for multiple dose oral administration. The microcapsules are easily wetted and suspended. The novel suspension may then be stored at the home of the patient in a common household refrigerator (i.e. at about 5° C.) and removed for oral administration at intervals over a period of up to about two weeks as directed by the patient's physician. The suspension should of course be well shaken before dispensing individual oral dosages. The reconstituted aqueous suspension will typically contain from about 100 to about 200 mg. bacampicillin acid addition salt per 5 ml. suspension. The above-mentioned dry powder may also, if desired, be distributed to the patient in, e.g., sachets for reconstitution with water for single dose oral administration. Reconstituted suspensions for single dose administration will typically be more dilute than those intended for multiple dose administration. Multiple dose formulation is of course preferred for reasons of convenience.

The dry powder for reconstitution may be prepared by blending the bacampicillin acid addition salt microcapsules with the other ingredients present in the reconstituted suspension by techniques well known to those skilled in the art of pharmaceutical production. The powder for reconstitution has good stability at room temperature, particularly if the bacampicillin acid addition salt microcapsules and other components of said powder have been dried carefully to remove moisture.

By "pharmaceutically acceptable" acid addition salts is meant those salts which are non-toxic at the dosages administered. The pharmaceutically acceptable water-soluble acid addition salts of bacampicillin which may be employed in the present invention include, for example, such salts as the hydrochloride, hydrobromide, sulfate, citrate, tartrate and maleate salts.

The bacampicillin acid addition salt microcapsules employed in the present invention are preferably prepared by an air suspension coating technique, such as the Wurster air suspension coating process disclosed in U.S. Pat. Nos. 3,117,027; 3,196,827; 3,241,520 and 3,253,944. In this process a bacampicillin acid addition salt powder is fluidized in a bed and a solution or suspension of ethyl cellulose and filler material in a volatile organic solvent, e.g. acetone, is sprayed into the bed. As droplets of this spray deposit upon the bacampicillin acid addition salt powder and the solvent evaporates, a coating builds up upon the bacampicillin acid addition salt powder core. The final size of the microcapsules is determined by the size of the fluidized bacampicillin acid addition salt powder plus the weight ratio of coating to said bacampicillin acid addition salt powder. The bacampicillin acid addition salt is preferably reduced to a less than 60 mesh size before being coated. When hydroxypropyl cellulose is utilized as the filler material and acetone is utilized as the volatile organic solvent, the bacampicillin acid addition salt powder is preferably fluidized with humidified 30°-50° C. air.

A preferred amount of coating is from about 25 weight percent to about 100 weight percent, based upon the weight of the acid addition salt core. Use of coating levels of less than about 25 weight percent necessitates reconstitution to a high dilution to maintain a palatable taste. Use of coating levels greater than about 100 weight percent is not preferred for economic reasons arising from the cost of the coating ingredients. A preferred size for the microcapsules is less than about 420 microns (i.e. microcapsules will pass through a 40 mesh screen). When hydroxypropyl cellulose is utilized as the filler material, an especially preferred amount of polymeric coating is from about 43 to about 67 weight percent, particularly about 54 weight percent, based upon the weight of the bacampicillin acid addition salt core. The preferred grade of ethyl cellulose for employment in the present invention is that having a viscosity of 10 cps., which can be dissolved at a high concentration in the acetone solution preferably used in the air suspension coating technique. The preferred grade of hydroxypropyl cellulose is that having a molecular weight of about 60,000. Suitable ethyl cellulose includes that sold under the tradename Ethocel (Dow Chemical Co.; Midland, Mich.) and suitable hydroxypropyl cellulose includes that sold under the tradename Klucel (Hercules Chemical Co.; Wilmington, Del.).

A critical parameter to the success of the present invention is the weight ratio of ethyl cellulose to filler material in the microcapsule coating. Thus, when the filler material is hydroxypropyl cellulose, it has been discovered that the ethyl cellulose to hydroxypropyl cellulose weight ratio in the coating must be maintained between from about 1.5:1 to about 2:1 to obtain the desired properties of the reconstituted oral suspension. Reducing this ratio below about 1.5:1 causes the taste-masking to become marginal, thus raising the possibility of rejection by the patient, while raising the ratio above about 2:1 reduces the bioavailability of the drug after oral administration.

To achieve suspension of the bacampicillin acid addition salt microcapsules after reconstitution with water, an adequate vehicle viscosity is usually obtained by introducing gums to the vehicle, e.g. xanthan gum. It is critical that the suspension medium have a pH at least 6.9 after reconstitution. When the suspension medium has a lower pH, taste-masking is found to be inadequate. The desired pH of the reconstituted suspension may be achieved with the use of buffering ingredients, e.g. sodium bicarbonate. It is a particularly surprising feature of the present invention that the reconstituted suspension exhibits good stability, thus permitting its use for multiple dose oral administration, even though the pH of the aqueous suspension medium is well above that at which stability problems for bacampicillin are known to begin in aqueous media.

By the term "pharmaceutically acceptable" aqueous suspension medium is meant a medium that is non-toxic at the dosages administered. In general, such a medium will have a pH less than about 9 and will be comprised of substances known to be safe for the intended use. In addition to the ingredients added to control viscosity and pH, the suspension medium may contain other ingredients well known to those skilled in the art of pharmaceutical production, e.g., suspension stabilizers, sugars, artificial sweeteners, flavoring ingredients, preservatives and particulate materials such as titanium dioxide to mask the visual appearance of the microcapsules. A preferred pH range for the suspension medium is from about 7.2 to about 8.2.

Although there is no intention to limit the scope of the invention in any way by the following discussion of mechanism, it appears that the invention operates in the following way. When the microcapsules are suspended in aqueous medium the water-soluble filler material, e.g. hydroxypropyl cellulose, is leached out of the coating leaving a multitude of pores connecting the active ingredient core with the aqueous medium. However, as the bacampicillin acid addition salt begins to diffuse out of these pores the leading edge thereof encounters the pH of the suspension medium (at least 6.9) and is converted to the water-insoluble free base. It is believed that this active ingredient material, which is converted to the free base within said pores, acts to plug up the pores and prevent substantial leaching of the active ingredient through the pores. Thus, the taste of the reconstituted suspension is palatable and the active ingredient is not exposed to a pH at which stability problems can occur. Nor does substantial leaching of the active ingredient occur in the mouth of the patient during the transient exposure to the neutral or slightly acidic pH's experienced therein. After the suspension is swallowed and reaches the more acidic regions of the gastrointestinal tract, however, the microcapsules are exposed to pH's at which the bacampicillin free base in the pores of the coating of the microcapsules is converted back to a water-soluble acid addition salt. The water-soluble acid addition salt of bacampicillin then floods from the core through the pores in the microcapsule coating and exhibits a high bioavailability to the patient.

A similar mechanism appears to operate when a water-permeable filler material, e.g. corn starch, is employed, whether or not such a filler material exhibits substantial solubility in water. The water-permeable filler material imparts a network of pores to the coating before reconstitution with water. After reconstitution with water, the free base active ingredient acts to plug up these pores and prevent substantial leaching through the pores. After the suspension is swallowed, the bacampicillin acid addition salt floods through the pores as described above.

Pharmaceutical suspensions of this invention were tested for bioavailability, taste-masking and stability. Bioavailability may be determined by measuring the mean blood serum ampicillin levels in a number of human or animal subjects periodically after oral administration. Maximum blood serum levels of ampicillin in humans are usually obtained between about 30 and about 60 minutes after oral administration of the suspension of the invention. In determining the effect of microcapsule coating parameters on bioavailability in vivo, it has been found that the human bioavailability results correlate well with an in vitro test in which the percentage of bacampicillin acid addition salt released after 15–60 minutes from a quantity of microcapsules suspended in water in a standard rotating bottle apparatus at 37° C. is measured. The equilibrium pH of the water in which the microcapsules are suspended is about 5.5, which is approximately the pH found in the duodenal region of the intestinal tract, the region of the intestinal tract immediately adjacent to the stomach.

Taste-masking may be determined by using human taste panels. Stability of the reconstituted formulation and the dry powder for reconstitution may be measured by standard techniques well known to those skilled in the art.

The following examples illustrate the invention but are not to be construed as limiting the same.

EXAMPLE 1

Preparation of Bacampicillin Hydrochloride Microcapsules

A solution was prepared containing 48 g./l. of ethyl cellulose (N.F., 10 cps.), 32 g./l. of hydroxypropyl cellulose (F.C.C., MW=60,000, Klucel EF) and the balance acetone (N.F.). The solution was then filtered through cheesecloth. Bacampicillin hydrochloride powder (sifted through 50 mesh screen, 940 g.) was then suspended in the granulating chamber of a Wurster air suspension coater with humidified 32° C. air and sprayed with the above filtered solution until a 35 wt. % coating, based upon the weight of bacampicillin hydrochloride, had been applied to the particles of bacampicillin hydrochloride. Said coating contained ethyl cellulose and hydroxypropyl cellulose in a 1.5:1 ratio by weight. The resulting microcapsules were then passed through a 40 mesh screen. The microcapsules (663 g.) were then dried under vacuum for 4 hours at 35° C. and then for another 16 hours under vacuum without application of heat.

EXAMPLE 2

Preparation of Dry Powder for Reconstitution

The following solid ingredients were blended for 30 minutes in a V-blender:

| | |
|---|---|
| Sodium bicarbonate (U.S.P.) | 31.4 g. |
| Mannitol (U.S.P.) | 334.5 g. |
| Sodium carboxymethyl cellulose (U.S.P.) | 31.4 g. |
| Xanthan gum (N.F.) | 62.7 g. |
| Titanium dioxide (U.S.P.) | 62.7 g. |
| Compressible sugar (N.F.) | 2194.0 g. |
| Wild cherry flavor (Food grade-artificial, spray dried) | 55.0 g. |
| Sodium benzoate (U.S.P.) | 31.4 g. |

The resulting blend was passed through a 40 mesh screen, blended again for 15 minutes in a V-blender, and then blended for 10 minutes in a V-blender with 158.8 g. of the bacampicillin hydrochloride microcapsules prepared in Example 1. The stability of this dry powder was 85% retained potency after 6 weeks at 50° C.

EXAMPLE 3

Preparation of Suspension for Oral Administration

The dry powder prepared in Example 2 was combined with water and the mixture shaken vigorously by hand to create an aqueous suspension for oral administration having a potency of 200 mg. bacampicillin hydrochloride per 10 ml. added water. This suspension had a pH of 7.6 and a stability of 89% retained potency after 14 days at 5° C.

EXAMPLE 4

Preparation of Dry Powder for Reconstitution

The following solid ingredients were weighed and blended for 30 minutes in a V-blender, after having been dried separately for 16 hours at 50° C. in a Stokes tray drier:

| | |
|---|---|
| Sodium bicarbonate (U.S.P.) | 77.5 g. |
| Mannitol (U.S.P.) | 837.5 g. |
| Sodium carboxymethyl cellulose (U.S.P.) | 25.0 g. |
| Xanthan gum (N.F.) | 50.0 g. |
| Titanium dioxide (U.S.P.) | 157.5 g. |
| Compressible sugar (N.F.) | 5480.0 g. |
| Sodium saccharin (N.F.) | 25.0 g. |

The blend was then passed through a Fitzpatrick mill to remove any lumps therein. The resulting material was blended for 30 minutes in a V-blender with 199.0 g. wild cherry flavor (food grade-artificial, spray dried) and 872.0 g. bacampicillin hydrochloride microcapsules—35 wt. % coating of ethyl cellulose: hydroxypropyl cellulose (1.5:1 ratio by weight), which microcapsules were prepared in like manner to that described in Example 1. The resulting blend was dried for 2 hours at 50° C. under vacuum.

The stability of this dry powder for reconstitution was 97% retained potency after 12 weeks at 50° C.

EXAMPLE 5

Preparation of Suspension for Oral Administration

In like manner to that described in Example 3, an aqueous suspension for oral administration was prepared from the dry powder for reconstitution prepared in Example 4. This suspension had a potency of 200 mg. bacampicillin hydrochloride per 5 ml. suspension, a pH of 7.4 and a stability of 95% retained potency after 14 days at 3°–5.5° C.

EXAMPLE 6

Preparation of Dry Powder for Reconstitution

In like manner to that described in Example 4, a blend of the following ingredients was prepared:

| | |
|---|---|
| Bacampicillin hydrochloride microcapsules - 35 wt. % coating of ethyl cellulose: hydroxypropyl cellulose (1.5:1 ratio by weight) - prepared in like manner to that described in Example 1 | 3864.0 g. |
| Sodium bicarbonate (U.S.P.) | 739.3 g. |
| Mannitol (U.S.P.) | 3580.0 g. |
| Sodium carboxymethyl cellulose (U.S.P.) | 107.0 g. |
| Xanthan gum (N.F.) | 214.0 g. |
| Titanium dioxide (U.S.P.) | 674.1 g. |
| Compressible sugar (N.F.) | 23460.0 g. |
| Sodium saccharin (N.F.) | 107.0 g. |
| Wild cherry flavor (Food grade - artificial, spray dried) | 882.4 g. |

EXAMPLE 7

Preparation of Suspension for Oral Administration

In like manner to that described in Example 3, an aqueous suspension for oral administration was prepared from the dry powder for reconstitution prepared in Example 6. This suspension had a potency of 125 mg. bacampicillin hydrochloride per 5 ml. suspension, a pH of 7.3 and a stability of 94% retained potency after 14 days at 3°–5.5° C.

EXAMPLE 8

Human Taste Panel Evaluation

Samples of the suspension to be evaluated were given to each of ten adults serving on the taste panel. The judges were asked to rate the taste of the suspension by assigning from 1 to 9 points according to the following scale: 9—like extremely; 8—like very much; 7—like moderately; 6—like slightly; 5—neither like nor dislike; 4—dislike slightly; 3—dislike moderately; 2—dislike very much; 1—dislike extremely. The total number of points assigned by the judges was divided by the number of judges to obtain the mean taste rating. A taste rating of 5.0 or higher is considered acceptable.

The following results were obtained using the above procedure:

| Suspension Prepared in Example Number | Mean Taste Rating |
|---|---|
| 3 | 5.4[a] |
| 5 | 5.7[b] |
| 7 | 6.1[b] |

[a]Taste evaluation made within 5 minutes after reconstitution.
[b]Taste evaluation made 30 minutes after reconstitution.

EXAMPLE 9

Bioavailability after Oral Administration

Twenty-one healthy male humans between 19 and 35 years of age and weighing 140 to 200 lbs. were each given oral administrations of 10 ml. of the suspension of Example 5, followed by about 6 oz. of water. Dosing was performed 30 minutes after reconstitution. Blood specimens were withdrawn from each subject at 0, 20, 40, 60, 80, 120, 240, 360 and 480 minutes after dosing. After clotting, blood serum was quickly separated from each specimen and stored at −20° C. until assayed for serum level of ampicillin by means of an automated microbiological agar diffusion assay. The mean peak serum ampicillin level for the twenty-one subjects was 6.7 micrograms/ml. at 40 minutes after dosing. A comparison test with 400 mg. bacampicillin HCl tablets gave a mean peak serum ampicillin level of 5.8 micrograms/ml. at 40 minutes after dosing.

EXAMPLE 10

Bioavailability after Oral Administration

In like manner to that described in Example 3, an aqueous suspension for oral administration having a potency of 400 mg, bacampicillin HCl per 30 ml. added water was prepared from the dry powder for reconstitution prepared in Example 2.

In like manner to that described in Example 9, a test with two groups of eight adult male human subjects gave a mean peak serum ampicillin level of 6.9 micrograms/ml. at 43 minutes after dosing with a quantity of said aqueous suspension (freshly reconstituted) containing 400 mg. bacampicillin HCl, compared to a mean peak serum ampicillin level of 6.4 micrograms/ml. at 60 minutes after dosing with a 400 mg. bacampicillin HCl tablet.

EXAMPLE 11

Bioavailability after Oral Administration

In like manner to that described in Example 9, a test with seven infant or small child subjects gave a mean peak serum ampicillin level of 14.4 micrograms/ml. at 60 minutes after dosing with a quantity of the suspension of Example 5 containing 28 mg. bacampicillin HCl/kg. body weight of the subject. This excellent result suggested the possibility of obtaining high serum ampicillin levels in pediatric applications with more dilute suspensions, e.g. the suspension of Example 7, thereby achieving an improved utilization of the active ingredient.

I claim:

1. A powder capable of being reconstituted by addition of water to yield a pharmaceutical suspension of bacampicillin acid addition salt microcapsules in an aqueous suspension medium, said powder comprising a mixture of bacampicillin acid addition salt microcapsules and a plurality of pharmaceutically acceptable suspension vehicle ingredients, said microcapsules comprising a core of a pharmaceutically acceptable, water-soluble acid addition salt of bacampicillin and a coating thereon consisting essentially of a mixture of a major portion of ethyl cellulose and a minor portion of a pharmaceutically acceptable, water-soluble or water-permeable filler material, said vehicle ingredients being such that the pH of the aqueous suspension medium in said reconstituted pharmaceutical suspension is at least 6.9, and the weight ratio of ethyl cellulose to said filler material in said coating being such that said pharmaceutical suspension has a stability of at least 85% retention of potency after 14 days at about 3° C., and provides an average maximum blood serum ampicillin level of at least about 6 micrograms/ml. after oral administration thereof to adult humans.

2. A powder of claim 1 wherein said filler material is an organic polymeric material.

3. A powder of claim 2 wherein said filler material is selected from the group consisting of hydroxypropyl cellulose, low substituted hydroxypropyl cellulose having a hydroxypropyl content of about 7 to 14 weight percent, methyl cellulose, hydroxypropyl methyl cellulose, polyethylene glycol, polyvinyl alcohol, carboxymethyl cellulose, polyvinyl pyrrolidone, gelatin, gum arabic and corn starch.

4. A powder capable of being reconstituted by addition of water to yield a pharmaceutical suspension of becampicillin acid addition salt microcapsules in an aqueous suspension medium, said powder comprising a mixture of bacampicillin acid addition salt microcapsules and a plurality of pharmaceutically acceptable suspension vehicle ingredients, said microcapsules comprising a core of a pharmaceutically acceptable, water-soluble acid addition salt of bacampicillin and a coating thereon consisting essentially of a mixture of ethyl cellulose and hydroxypropyl cellulose in a weight ratio of from about 1.5:1 to about 2:1, and said vehicle ingredients being such that the pH of the aqueous suspension medium in said reconstituted pharmaceutical suspension is at least 6.9, whereby said pharmaceutical suspension has a stability of at least 85% retention of potency after 14 days at about 3° C.

5. A powder of claim 1 or 4 wherein said acid addition of bacampicillin is bacampicillin hydrochloride.

6. A powder of claim 4 wherein said vehicle ingredients are such that the pH of the aqueous suspension medium in said pharmaceutical suspension is from about 7.2 to about 8.2.

7. A powder of claim 1 or 4 wherein the weight of said coating is from about 25 to about 100 percent of the weight of said core of bacampicillin acid addition salt.

8. A powder of claim 6 wherein the weight ratio of ethyl cellulose to hydroxypropyl cellulose in said coating is about 1.5:1 and the weight of said coating is about 54 percent of the weight of said core of bacampicillin acid addition salt.

9. A powder of claim 1 wherein said vehicle ingredients are such that the pH of the aqueous suspension medium in said pharmaceutical suspension is from about 7.2 to about 8.2.

10. An aqueous pharmaceutical suspension prepared by admixing a powder of claim 1 or 4 with water.

11. A pharmaceutical suspension of claim 10 wherein said acid addition salt of bacampicillin is bacampicillin hydrochloride.

12. A pharmaceutical suspension of claim 11 containing from about 20 to about 40 mg. bacampicillin hydrochloride per ml. of said suspension.

* * * * *

UNITED STATES PATENT AND TRADEMARK OFFICE
CERTIFICATE OF CORRECTION

PATENT NO. : 4,321,253
DATED : March 23, 1982
INVENTOR(S) : Morgan L. Beatty

It is certified that error appears in the above-identified patent and that said Letters Patent are hereby corrected as shown below:

On front page of patent after title, change

"[76] Inventor: Morgan L. Beatty, Pfizer Inc., 235 E. 42nd St., New York, N.Y. 10017"

to

--[75] Inventor: Morgan L. Beatty, Waterford, Conn.

[73] Assignee: Pfizer Inc., New York, N.Y.--.

Claim 5, column 10, line 8, insert --salt-- after "tion".

Signed and Sealed this

Eighth Day of June 1982

|SEAL|

Attest:

GERALD J. MOSSINGHOFF

*Attesting Officer*  *Commissioner of Patents and Trademarks*